US006379892B1

(12) United States Patent
Kacena

(10) Patent No.: US 6,379,892 B1
(45) Date of Patent: Apr. 30, 2002

(54) METHODS, KITS AND COMPOSITIONS OF MATTER USEFUL FOR DETERMINING *CHLAMYDIA PNEUMONIAE*

(75) Inventor: Katherine Kacena, Waltham, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/573,377

(22) Filed: May 18, 2000

(51) Int. Cl.[7] .......................... C12Q 1/68; C12P 19/34; C07H 21/04

(52) U.S. Cl. ......................... 435/6; 435/91.1; 435/91.2; 536/24.32; 536/24.31; 536/24.3; 536/24.33

(58) Field of Search .......................... 536/24.32, 24.31, 536/24.3, 24.33; 435/91.1, 91.2, 6

(56) References Cited

U.S. PATENT DOCUMENTS

| | | | | |
|---|---|---|---|---|
| 5,281,518 A | | 1/1994 | Campbell et al. | 436/6 |
| 5,350,673 A | | 9/1994 | Campbell et al. | 435/6 |
| 5,595,874 A | * | 1/1997 | Hogan et al. | 435/6 |

OTHER PUBLICATIONS

Quinn, Thomas C., *Infectious Diseases* 11:301–307 (1998).

Campbell, Lee Ann et al., *J. of Clin. Microbio.* 30:434–439 (1992).

Kikuta, Lynne C. et al., *Infection and Immunity*, 59:4665–4669 (1991).

Walker, G. Terrance et al., Nat'l. Acad. Sci, 89:392–396 (1992).

Walker, G. Terrance et al., Nucleic Acids Res., 7:1691–1696 (1992).

* cited by examiner

*Primary Examiner*—Jeffrey Fredman
*Assistant Examiner*—Juliet Einsmann
(74) *Attorney, Agent, or Firm*—David W. Highet

(57) ABSTRACT

Amplification primers and methods for specific amplification and detection of *Chlamydia pneumoniae* are disclosed. The primer-target binding sequences are useful for amplification and detection of *Chlamydia pneumonia* target in a variety of amplification and detection reactions.

32 Claims, 1 Drawing Sheet

```
C. pneumoniae  X60068 CCTTTCGAAGTTCAAGTTGGCGATATCATTTTAATGGATAAGTATGCAGGT
C. psittaci    X51404 .....T......ACC..G..T....CTG.......A.....A..C..G..A
C. trachomatis M31739 .....T........G.....T..C...G.......T.....A...T.T..C
C. muridarum   U52049 .....T........G........C...G.......T.........T.T..C

X60068       CAAGAAATCACAATCGATGACGAAGAGTATGTCATTCTACAGTCCAGTGAAATCATGGCC
X51404       ......C.T..CG.T....GT..G.....C......G.T...GAA..C...G.T.....A
M31739       ......C.T..T.....A.GT........C.....CG.T..AATG..C...G.T..C..A
U52049       ......C....TG....A.GT.....A........CG.T..AATG..C...G.T..A..A

X60068       GTCCTAAAATAA****AATACTAGTTTGCAGATTATAGAAAGTTAAGGAGA
X51404       ..T..C..G...GAGA...CA.TA...AT.....GC.A............C
M31739       .....GC.....A**A.C..AG..AG..*.AG*****A.G.T........C
U52049       .....GC.....A**A....AG..AG..*.AG.****A.G.T........C
```

Figure 1

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<221> NAME/KEY: misc_feature
<222> LOCATION: (18)..(23)
<223> OTHER INFORMATION: BsoBI restriction site.
<223> OTHER INFORMATION: Description of Artificial Sequence:The 5' and
3' ends are complementary to Chlamydia pneumoniae
X60068 and 6 bases in the mid dle are a BsoBI
restriction site.

<400> SEQUENCE: 1
aatggataag tatgcagctc gggaaatcac aa 32

<210> SEQ ID NO 2
<211> LENGTH: 31
<212> TYPE: DNA
<213> ORGANISM: Artificial Sequence
<220> FEATURE:
<221> NAME/KEY: misc_feature
<222> LOCATION: (19)..(24)
<223> OTHER INFORMATION: BsoBI restriction site.
<223> OTHER INFORMATION: Description of Artificial Sequence:The 5' and
3' ends are complementary to Chlamydia pneumoniae
X60068 and 6 bases in the mid dle are a BsoBI
restriction site.

<400> SEQUENCE: 2
ttaggacggc catgatttct cgggactgta g 31

<210> SEQ ID NO 3
<211> LENGTH: 16
<212> TYPE: DNA
<213> ORGANISM: Chlamydia pneumoniae

<400> SEQUENCE: 3
caagttggct atatca 16

<210> SEQ ID NO 4
<211> LENGTH: 17
<212> TYPE: DNA
<213> ORGANISM: Chlamydia pneumoniae

<400> SEQUENCE: 4
tctccttaac tttctat 17

<210> SEQ ID NO 5
<211> LENGTH: 32
<212> TYPE: DNA
<213> ORGANISM: Chlamydia pneumoniae
<220> FEATURE:
<221> NAME/KEY: misc_feature
<222> LOCATION: (1)
<223> OTHER INFORMATION: This nucleotide is lab eled with FAM.
<221> NAME/KEY: misc_feature
<222> LOCATION: (9)
<223> OTHER INFORMATION: This nucleotide is lab eled with Dabcyl.

<400> SEQUENCE: 5
tacccgagtt cgatgacgaa gagtatgtca tt 32

<210> SEQ ID NO 6

-continued

```
<211> LENGTH: 41
<212> TYPE: DNA
<213> ORGANISM: Artificial Sequence
<220> FEATURE:
<221> NAME/KEY: misc_feature
<222> LOCATION: (19)..(24)
<223> OTHER INFORMATION: BsoBI restriction site.
<223> OTHER INFORMATION: Description of Artificial  Sequence:The 5' and
      3' ends are complementary to Chlamydia pneumoniae
      X60068 and 6 bases in the mid dle are a BsoBI
      restriction site.

<400> SEQUENCE: 6

cgattccgct ccagacttct cgggaggtca agaaatcaca a                          41


<210> SEQ ID NO 7
<211> LENGTH: 42
<212> TYPE: DNA
<213> ORGANISM: Artificial Sequence
<220> FEATURE:
<221> NAME/KEY: misc_feature
<222> LOCATION: (19)..(24)
<223> OTHER INFORMATION: BsoBI restriction site.
<223> OTHER INFORMATION: Description of Artificial  Sequence:The 5' and
      3' ends are complementary to Chlamydia pneumoniae
      X60068 and 6 bases in the mid dle are a BsoBI
      restriction site.

<400> SEQUENCE: 7

accgcatcga atgcatgtct cggggatttc actggactgt ag                         42


<210> SEQ ID NO 8
<211> LENGTH: 15
<212> TYPE: DNA
<213> ORGANISM: Chlamydia pneumoniae

<400> SEQUENCE: 8

ttaatggata agtat                                                       15


<210> SEQ ID NO 9
<211> LENGTH: 15
<212> TYPE: DNA
<213> ORGANISM: Chlamydia pneumoniae

<400> SEQUENCE: 9

ttttatttta ggacg                                                       15


<210> SEQ ID NO 10
<211> LENGTH: 39
<212> TYPE: DNA
<213> ORGANISM: Chlamydia pneumoniae
<220> FEATURE:
<221> NAME/KEY: misc_feature
<222> LOCATION: (1)
<223> OTHER INFORMATION: This nucleotide is lab eled with FAM.
<221> NAME/KEY: misc_feature
<222> LOCATION: (16)
<223> OTHER INFORMATION: This nucleotide is lab eled with Dabcyl.

<400> SEQUENCE: 10

tagcacccga gtgctttcga tgacgaagag tatgtcatt                             39


<210> SEQ ID NO 11
<211> LENGTH: 43
<212> TYPE: DNA
<213> ORGANISM: Artificial Sequence
<220> FEATURE:
<221> NAME/KEY: misc_feature
<222> LOCATION: (22)..(27)
```

-continued

```
<223> OTHER INFORMATION: BsoBI restriction site.
<223> OTHER INFORMATION: Description of Artificial  Sequence:The 5' and
      3' ends are complementary to Chlamydia pneumoniae
      X60068 and 6 bases in the mid dle are a BsoBI
      restriction site.

<400> SEQUENCE: 11

gatatcattt taatggataa gctcgggggt caagaaatca caa                    43


<210> SEQ ID NO 12
<211> LENGTH: 42
<212> TYPE: DNA
<213> ORGANISM: Artificial Sequence
<220> FEATURE:
<221> NAME/KEY: misc_feature
<222> LOCATION: (21)..(26)
<223> OTHER INFORMATION: BsoBI restriction site.
<223> OTHER INFORMATION: Description of Artificial  Sequence:The 5' and
      3' ends are complementary to Chlamydia pneumoniae
      X60068 and 6 bases in the mid dle are a BsoBI
      restriction site.

<400> SEQUENCE: 12

agtattttat tttaggacgg ctcgggtttc actggactgt ag                     42


<210> SEQ ID NO 13
<211> LENGTH: 18
<212> TYPE: DNA
<213> ORGANISM: Chlamydia pneumoniae

<400> SEQUENCE: 13

cctttcgaag ttcaagtt                                                18


<210> SEQ ID NO 14
<211> LENGTH: 17
<212> TYPE: DNA
<213> ORGANISM: Chlamydia pneumoniae

<400> SEQUENCE: 14

tctccttaac tttctat                                                 17


<210> SEQ ID NO 15
<211> LENGTH: 32
<212> TYPE: DNA
<213> ORGANISM: Chlamydia pneumoniae
<220> FEATURE:
<221> NAME/KEY: misc_feature
<222> LOCATION: (1)
<223> OTHER INFORMATION: This nucleotide is lab eled with FAM.
<221> NAME/KEY: misc_feature
<222> LOCATION: (9)
<223> OTHER INFORMATION: This nucleotide is lab eled with Dabcyl.

<400> SEQUENCE: 15

tacccgagtt cgatgacgaa gagtatgtca tt                                32


<210> SEQ ID NO 16
<211> LENGTH: 158
<212> TYPE: DNA
<213> ORGANISM: Chlamydia pneumoniae

<400> SEQUENCE: 16

cctttcgaag ttcaagttgg cgatatcatt ttaatggata agtatgcagg t caagaaatc     60

acaatcgatg acgaagagta tgtcattcta cagtccagtg aaatcatggc c gtcctaaaa    120

taaaatacta gtttgcagat tatagaaagt taaggaga                         158
```

METHODS, KITS AND COMPOSITIONS OF MATTER USEFUL FOR DETERMINING *CHLAMYDIA PNEUMONIAE*

FIELD OF THE INVENTION

The present invention relates to methods for determining the presence, absence or amount of *Chlamydia pneumoniae* producing organisms in specimens, including specimens from animals, humans and culture. The method involves using nucleic acid primers to amplify specifically a *Chlamydia pneumoniae* target, preferably using one of the techniques of Strand Displacement Amplification (SDA), thermophilic Strand Displacement Amplification (tSDA) or fluorescent real time tSDA.

BACKGROUND OF THE INVENTION

*Chlamydia pneumoniae* is an intracellular microorganism which is difficult to isolate by culture. Evidence has accrued showing the relationship between heart disease and infection with *Chlamydia pneumoniae*. The worldwide burden from cardiovascular disease measured in disability adjusted life years (DALYs) is greater than either HIV or STDs. *Chlamydia pneumoniae* is responsible for about 20% of cases of community-acquired pneumonia (CAP). Nucleic acid amplification is a powerful technology, which allows rapid detection of specific target sequences. The oligonucleotide primers of the present invention are applicable to nucleic acid amplification and detection of *Chlamydia pneumoniae.*

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *Proc. Natl. Acad. Sci. USA* 89:392–396 and 1992 *Nucl. Acids Res.* 20:1691–1696). Alternatively, to avoid using a hemimodified recognition site, a recognition site for a nicking enzyme may be used rather than the restriction endonuclease recognition site. The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For example, amplification of a target sequence according to the invention using the Polymerase Chain Reaction (PCR) will employ amplification primers consisting of the target binding sequences of the amplification primers described herein. For amplification methods that require specialized sequences appended to the target other than the nickable restriction endonuclease recognition site and the tail of SDA (e.g., an RNA polymerase promoter for Self-Sustained Sequence Replication (3SR), Nucleic Acid Sequence-Based Amplification (NASBA) or the Transcription-Based Amplification System (TAS)), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization to a species of organism or a group of related species without substantial detection, amplification or oligonucleotide hybridization to other species of the same genus or species of a different genus.

The term assay probe refers to any oligonucleotide used to facilitate detection or identification of a nucleic acid. Detector probes, detector primers, capture probes, signal primers and reporter probes as described below are examples of assay probes.

The term amplicon refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not imply the presence of exponentially amplified nucleic acids.

SUMMARY OF THE INVENTION

The present invention provides oligonucleotide primers that can be used for amplification of a target sequence found in *Chlamydia pneumoniae*. More specifically, the target sequence comprises segments of the *Chlamydia pneumoniae* groES-EL gene. The amplification primers have been designed for high-efficiency, high-specificity amplification at elevated temperatures, such as in tSDA and the PCR, however, they are also useful in lower-temperature amplification reactions such as conventional SDA, 3SR or NASBA. Oligonucleotide assay probes that hybridize to the assay region of the amplified target are used to detect the amplification products.

The oligonucleotides of the invention may be used after culture as a means for confirming the identity of the cultured organism. Alternatively, they may be used with clinical samples from humans or animals, such as sputum, tissue and peripheral blood mononuclear cells, or with samples of contaminated food or water for detection and identification of *Chlamydia pneumoniae* nucleic acid using known amplification methods. In either case, the inventive oligonucleotides and assay methods provide a means for rapidly discriminating between *Chlamydia pneumoniae* and other microorganisms, allowing the practitioner to identify this microorganism rapidly without resorting to the more traditional procedures customarily relied upon. Such rapid identification of the specific etiological agent involved in an infection provides information that can be used to determine appropriate action within a short period of time.

BRIEF DESCRIPTION OF THE DRAWING

FIG. 1 shows an alignment of the GroES-EL gene from *C. pneumoniae* with the corresponding gene from *C. psittaci, C. trachomatis* and *C. muridarum*. The GenBank Accession Numbers are listed after the name of the organism. Only differences from *C. pneumoniae* are shown. The symbol "*" is used for spacing purposes to show the best alignment between the different sequences with nucleotides on either side of the symbol being consecutive bases in the sequence. The sequence for *C. pneumoniae* X60068 is shown in the Sequence Listing as SEQ ID NO:16.

SUMMARY OF THE SEQUENCES

SEQ ID NOs:1, 6 and 11 are sequences of oligonucleotides used as upstream primers or target binding sequences of upstream primers for amplification of the *Chlamydia pneumoniae* groES-EL gene. SEQ ID NOs:2, 7 and 12 are sequences of oligonucleotides used as downstream primers or target binding sequences of downstream primers for amplification of the *Chlamydia pneumoniae* groES-EL gene. SEQ ID NOs:3, 8 and 13 are the sequences of oligonucleotides used as upstream bumpers for SDA amplification of the groES-EL gene. SEQ ID NOs:4, 9 and 14 are the sequences of oligonucleotides used as downstream bumpers for SDA amplification of the groES-EL gene. SEQ ID NOs:5, 10 and 15 are sequences of detector oligonucleotides (probes or reporters) for the *Chlamydia pneumoniae* groES-EL gene.

SEQ ID NO:16 is a sequence from *C. pneumoniae* as shown in FIG. 1.

DETAILED DESCRIPTION OF THE INVENTION

The present invention relates to oligonucleotides, amplification primers and assay probes which exhibit *Chlamydia pneumoniae*-specificity in nucleic acid amplification reactions. Also provided are methods for detecting and identifying *Chlamydia pneumoniae* nucleic acids using the oligonucleotides of the invention. The preferred methods are to use SDA, tSDA or homogeneous real time fluorescent tSDA. These methods are known to those skilled in the art from references such as U.S. Pat. Nos. 5,547,861, 5,648,211, 5,846,726 and 5,928,869, the disclosures of which are hereby specifically incorporated herein by reference.

The primers of the present invention were designed based on an analysis of *Chlamydia pneumoniae* gene sequence data as aligned with other Chlamydia sequence data. These alignments are shown in FIG. 1. Primers developed for use in tSDA are shown in Table 1. Also shown are probes for the detection of the resultant amplicons. The exemplary restriction endonuclease recognition sites (BsoBI) in the amplification primers are shown in boldface type and the target binding sequences are italicized. The target binding sequence of an amplification primer determines its target specificity. Three sets of primers bumpers and detectors are set forth. The set referred to as "3'-end positioned restriction site" consists of SEQ ID NOs:1–5, the set referred to as "universal tail" consists of SEQ ID NOs:6–10, and the set referred to as "restriction site centered" consists of SEQ ID NOs:11–15.

TABLE 1

| Amplification Oligonucleotides | |
|---|---|
| Upstream Primers | |
| groEs-EL-3: 5'-*AATGGATAAGTATGCAG***CTCGGG***AAATCACAA*-3' | (SEQ ID 1) |
| groES-EL-U: 5'-CGATTCCGCTCCAGACTT**CTCGGG***AGGTCAAGAAATCACAA*-3' | (SEQ ID 6) |
| groES-EL-R: 5'-*GATATCATTTTAATGGATAAG***CTCGGG***GGTCAAGAAATCACAA*-3' | (SEQ ID 11) |
| Downstream Primers | |
| groES-EL-3: 5'-*TTAGGACGGCCATGATTT***CTCGGG***ACTGTAG*-3' | (SEQ ID 2) |
| groES-EL-U: 5'-ACCGCATCGAATGCATGT**CTCGGG***GATTTCACTGGACTGTAG*-3' | (SEQ ID 7) |
| groES-EL-R: 5'-*AGTATTTTATTTTAGGACGG***CTCGGG***TTTCACTGGACTGTAG*-3' | (SEQ ID 12) |
| Upstream Bumper | |
| groES-EL-3: 5'-CAAGTTGGCTATATCA-3' | (SEQ ID 3) |
| groES-EL-U: 5'-TTAATGGATAAGTAT-3' | (SEQ ID 8) |
| groES-EL-R: 5'-CCTTTCGAAGTTCAAGTT-3' | (SEQ ID 13) |
| Downstream Bumper | |
| groES-EL-3: 5'-TCTCCTTAACTTTCTAT-3' | (SEQ ID 4) |
| groES-EL-U: 5'-TTTTATTTTAGGACG-3' | (SEQ ID 9) |
| groES-EL-R: 5'-TCTCCTTAACTTTCTAT-3' | (SEQ ID 14) |
| Detector Probes | |
| groES-EL-3: 5'-(T-FAM)ACCCGAG(T-Dabcyl)TCGATGACGAAGAGTATGTCATT-3' | (SEQ ID 5) |
| groES-EL-U: 5'-(T-FAM)AGCACCCGAGTGCT(T-Dabcyl)TCGATGACGAAGAGTATGTCATT-3' | (SEQ ID 10) |
| groEs-EL-R: 5'-(T-FAM)ACCCGAG(T-Dabcyl)TCGATGACGAAGAGTATGTCATT-3' | (SEQ ID 15) |

It should be noted that the 3 upstream primers all end in the same sequence of 9 nucleotides and the 3 downstream primers all end in the same sequence of 7 nucleotides. The groES-EL-U primers have universal tails at their 5' ends. The groES-EL-3 and groES-EL-U detector probes have only 7 nucleotides between the T-FAM and T-dabcyl and because of this closeness do not require a hairpin for detection. The groES-EL-U detector probe has 14 nucleotides separating T-Fam and T-dabcyl and the 5 nucleotides at each end of this region can form a hairpin structure with 4 unpaired nucleotides in the center of the hairpin.

As nucleic acids do not require complete complementarity in order to hybridize, it is to be understood that the probe and primer sequences herein disclosed may be modified to some extent without loss of utility as *Chlamydia pneumoniae*-specific probes and primers. As is known in the art, hybridization of complementary and partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization conditions to maintain *Chlamydia pneumoniae*-specificity require only routine experimentation and are within the ordinary skill in the art.

The amplification products generated using the primers disclosed herein may be detected by a characteristic size, for example, on polyacrylamide or agarose gels stained with ethidium bromide. Alternatively, amplified target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al. (1992, *Nucl. Acids* Res. 20:1691–1696) (a detector primer) or by hybridization, extension and conversion to double stranded form as described in EP 0 678 582 (a signal primer). Preferably, the assay probe is selected to hybridize to a sequence in the target that is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label that requires additional reagents to render it detectable. Indirectly detectable labels include, for example, chemiluminescent agents, enzymes that produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for specific detection and identification of nucleic acids may be packaged in the form of a kit. Typically, such a kit contains at least one pair of amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers confer species hybridization specificity on the oligonucleotides and therefore provide species specificity to the amplification reaction. Thus, the target binding sequences of the amplification primers of the invention are also useful in other nucleic acid amplification protocols such as the PCR, conventional SDA (a reaction scheme which is essentially the same as that of tSDA but conducted at lower temperatures using mesophilic enzymes), 3SR, NASBA and TAS. Specifically, any amplification protocol which utilizes cyclic, specific hybridization of primers to the target sequence, extension of the primers using the target sequence as a template and separation or displacement of the extension products from the target sequence may employ the target binding sequences of the invention. For amplification methods that do not require specialized, non-target binding sequences (e.g., PCR), the amplification primers may consist only of the target binding sequences of the amplification primers listed in Table 1.

Other sequences, as required for performance of a selected amplification reaction, may optionally be added to the target binding sequences disclosed herein without altering the species specificity of the oligonucleotide. By way of example, the specific amplification primers may contain a recognition site for the restriction endonuclease BsoBI which is nicked during the SDA reaction. It will be apparent to one skilled in the art that other nickable restriction endonuclease recognition sites may be substituted for the BsoBI recognition site including, but not limited to, those recognition sites disclosed in EP 0 684 315. Preferably, the recognition site is for a thermophilic restriction endonuclease so that the amplification reaction may be performed under the conditions of tSDA. Similarly, the tail sequence of the amplification primer (5' to the restriction endonuclease recognition site) is generally not critical, although the restriction site used for SDA and sequences which will hybridize either to their own target binding sequence or to the other primers should be avoided. Some amplification primers for SDA therefore consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions (e.g., 3SR, NASBA and TAS), the amplification primers may consist of the target binding sequence and additional sequences required for the selected amplification reaction (e.g., sequences required for SDA as described above or a promoter recognized by RNA polymerase for 3SR). Adaptation of the target binding sequences of the invention to amplification methods other than SDA employs routine methods for preparation of amplification primers, such as chemical synthesis, and the well known structural requirements for the primers of the selected amplification reaction. The target binding sequences of the invention may therefore be readily adapted to *Chlamydia pneumoniae*-specific target amplification and detection in a variety of amplification reactions using only routine methods for production, screening and optimization.

In SDA, the bumper primers are not essential for species specificity, as they function to displace the downstream, species-specific amplification primers. It is required only that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence.

Amplification reactions employing the primers of the invention may incorporate thymine as taught by Walker, et al. (1992, *Nucl. Acids Res.* 20:1691–1696), or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (UGI) prior to performing the subsequent amplification to prevent excision of dU in newly-formed amplification products.

SDA is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (α-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having selected restriction endonuclease recognition/cleavage sites for nicking in the SDA reaction be generated as described by Walker, et al. (1992, *Nucl Acids Res.* 20:1691–1696) and in U.S. Pat. No. 5,270,184 (herein incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with UGI prior to amplification of the target. Alternatively, UDG may be heat-inactivated. In tSDA, the higher temperature of the reaction itself (≧50° C.) can be used concurrently to inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity of the restriction enzyme is also of great importance, as it is nicking which perpetuates the reaction and allows subsequent rounds of target amplification to initiate.

tSDA is performed essentially as the conventional SDA described by Walker, et al. (1992, *Proc. Natl. Acad. Sci. USA* 89:392–396 and 1992, *Nucl. Acids Res.* 20:1691–1696), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in tSDA are BsrI, BstNI, BsmAI, BslI and BsoBI (New England BioLabs), and BstOI (Promega). The preferred thermophilic polymerases are Bca (Panvera) and Bst (New England BioLabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises both a single-stranded 5' or 3' section which hybridizes to the target sequence (the target binding sequence), as well as an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

When added to the amplification reaction, the detector oligonucleotide signal primers of the invention are converted to double-stranded form by hybridization and extension as described above. Strand displacement by the polymerase also unfolds or linearizes the secondary structure and converts it to double-stranded from by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as: a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo$^-$Vent or exo$^-$ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease that remains active through the high temperature phases of the PCR reaction could be present during amplification to provide a real-time assay. As in SDA systems, separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample that may interfere with detection of the signal or other aspects of the assay.

EXAMPLES

The following Examples illustrate specific embodiments of the invention described herein. As would be apparent to skilled artisans, various changes and modifications are possible, and are contemplated within the scope of the invention described.

EXAMPLE 1 t-SDA Reaction Conditions for *Chlamydia pneumoniae* GroES-EL Primers

A. 3' End Positioned Restriction Site Primers (GroES-EL-3)

The amplification reactions were conducted at 52.5° C. in 100 μL of buffer containing final concentrations of the following components: 100 mM Bicine—61.4 mM KOH (pH 8.8 for the Bicine-KOH stock solution), 20 mM potassium phosphate (pH 7.6), 1.86% trehalose, 10 μg acetylated bovine serum albumin, 0.36 mM dithiothreitol, 0.1 mM dATP, 0.1 mM dTTP, 0.1 mM dGTP, 0.7 mM 2'-deoxycytidine 5'-O-(1-thiotriphosphate), 0.5 μM primer 1, 0.5 μM primer 2, 0.05 μM bumper 1, 0.05 μM bumper 2, 0.2 μM detector, 5 mM magnesium acetate, 1000 ng human placental DNA, 6 units Bst polymerase, and 27 units BsoBI. One Bst polymerase unit here is defined as the quantity of enzyme required to incorporate one nanomole of the nucleotide-dGTP into a defined polymerization template in one minute. The 6 units of Bst polymerase are equal to 35 units of the enzyme as defined by New England Biolabs. One BsoBI unit is defined as the quantity of enzyme required to release by nicking, one picomole of a defined oligonucleotide hybrid in one minute. The 27 units of BsoBI used here are equal to 490 units as defined by New England Biolabs.

In brief 50 μL of primer-bumper-detector mix was placed into a well of a microtiter plate. To this was added 100 μL of the process specimen. The solution was mixed by pipetting up and down one time. The plate was placed on a hotplate at 95° C. for 5 minutes. 100 μL of this mix was transferred to an amplification plate at 52.5° C. Amplification was carried out for 1 hour at a constant temperature of 52.5° C. The assay was also performed and worked at 60° C. and with up to at least 5% DMSO.

B. Universal Tail Primers (GroES-EL-U)

The amplification reactions were conducted at 52.5° C. in 100 μL of buffer containing final concentrations of the following components: 100 mM Bicine—61.4 mM KOH (pH 8.8 for the Bicine-KOH stock solution), 5% dimethylsulfoxide (DMSO), 9.5% glycerol, 20 mM potassium phosphate (pH 7.6), 1.86% trehalose, 10 μg acetylated bovine serum albumin, 0.36 mM dithiothreitol, 0.1 mM dATP, 0.1 mM dTTP, 0.1 mM dGTP, 0.7 mM 2'-deoxycytidine 5'-O-(1-thiotriphosphate), 0.5 μM primer 1, 0.5 μM primer 2, 0.05 μM bumper 1, 0.05 μM bumper 2, 0.2 μM detector, 5 mM magnesium acetate, 1000 ng human placental DNA, 6 units Bst polymerase, and 27 units BsoBI. The reactions were performed as described above for the 3' end positioned primers. This reaction was successfully performed at 60° C. and also in the absence of glycerol.

C. Restriction Site Centered Primers (GroES-EL-R)

Reactions using the restriction site centered primers were performed using the same conditions as used for the 3' end positioned restriction site primers.

EXAMPLE 2

Sensitivity of GroES-EL Primers

Reactions were performed as in Example 1. The primers, bumpers and detector used were for the Universal Tail Primers (GroES-EL-U). Sixteen reactions were performed for each level of target. The raw data for these experiments are shown in Table 2. The data was then analyzed to determine whether each sample was positive or negative and the final results are summarized in Table 3. It is seen that positive results were seen consistently at levels of 50 elementary bodies (EB) of *Chlamydia pneumoniae* or greater and in 15 of 16 samples at a level of 10 EB. Six of 16 samples gave positive results at levels of 2.5 or 5 EB and all control samples using zero EB tested negative.

The distinction between a positive and negative result is based upon testing 20 samples which are known to be negative for *Chlamydia pneumoniae*, determining the mean and standard deviation of these samples, and setting a cutoff value for a positive result to be a sample which is at least 3 standard deviations greater than the mean of the negative controls. Here the negative control was human placental DNA.

TABLE 2

| Neg. Control | 2.5 EB | 5 EB | 10 EB | 50 EB | 200 EB |
|---|---|---|---|---|---|
| 592 | 762 | 1768 | 3892 | 22135 | 26263 |
| 725 | 936 | 572 | 15850 | 28517 | 41785 |
| 1344 | 359 | 546 | 16278 | 20327 | 35292 |
| 490 | 738 | 9744 | 3371 | 33443 | 26317 |
| 384 | 20003 | 884 | 24021 | 32501 | 40036 |
| 315 | 838 | 17724 | 23818 | 29392 | 25524 |
| 849 | 177 | 15243 | 5373 | 25841 | 41656 |
| 301 | 931 | 408 | 8471 | 19125 | 26099 |
| 667 | 337 | 84 | 16773 | 30253 | 25585 |
| 1235 | 3735 | 283 | 972 | 26296 | 30734 |
| 650 | 8191 | 531 | 9401 | 32170 | 25263 |
| 571 | 317 | 722 | 8759 | 17099 | 32361 |
| 434 | 490 | 383 | 9034 | 15720 | 32689 |
| 285 | 14938 | 16372 | 10321 | 25379 | 30835 |
| 511 | 2453 | 1014 | 6364 | 20154 | 25852 |
| 393 | 17486 | 5844 | 2046 | 21783 | 40162 |

TABLE 3

| Target EB | Test Negative | Test Positive |
|---|---|---|
| 0 | 16 | 0 |
| 2.5 | 10 | 6 |
| 5 | 10 | 6 |
| 10 | 1 | 15 |
| 50 | 0 | 16 |
| 200 | 0 | 16 |

By fitting the data to a curve it was determined that the estimated level of detection is 14.81 EBs/reaction with 95% confidence limits.

A similar set of assays was performed as above, but instead of the Universal Primer set, the 3' end positioned restriction site set (GroES-EL-3) of primers, bumpers and detector were used. The raw data are shown in Table 4. A cutoff value of 2000 was used. Samples equal to or below this value were considered negative and those above this were positive. The negative samples are highlighted in the columns which had *Chlamydia pneumoniae* samples in them.

TABLE 4

| Neg. control | 2.5 EB | 5 EB | 10 EB | 20 EB | 50 EB |
|---|---|---|---|---|---|
| 852 | 2411 | 1436 | 5391 | 13378 | 11776 |
| 277 | 12304 | 681 | 2165 | 9443 | 19150 |
| 939 | 1744 | 2113 | 1967 | 13779 | 17279 |
| 967 | 973 | 8479 | 4516 | 4770 | 19193 |
| 1187 | 4394 | 6311 | 11312 | 17254 | 17682 |
| 608 | 7288 | 1863 | 12324 | 17624 | 18682 |

TABLE 4-continued

| Neg. control | 2.5 EB | 5 EB | 10 EB | 20 EB | 50 EB |
|---|---|---|---|---|---|
| 1157 | 2461 | 2715 | 980 | 10065 | 22128 |
| 488 | 1227 | 644 | 5691 | 8063 | 19966 |
| 59 | 1175 | 1535 | 16683 | 4440 | 15074 |
| 374 | 958 | 5219 | 8275 | 7591 | 14318 |
| 613 | 2419 | 3998 | 3542 | 10279 | 15483 |
| 635 | 2127 | 1606 | 2441 | 10880 | 21321 |
| 777 | 1669 | 940 | 5664 | 7774 | 16950 |
| 921 | 647 | 5495 | 10536 | 6239 | 18525 |
| 950 | 850 | 1830 | 4462 | 13883 | 17670 |
| 548 | 11473 | 1663 | 6688 | 16411 | 15430 |

EXAMPLE 3

Strain Sensitivity

The sensitivity of the assay across different strains of Chlamydia pneumoniae was tested. Assays were performed as in Example 1. The primers, detectors and bumpers used were the 3' end positioned restriction set (GroES-EL-3). Each strain of Chlamydia pneumoniae was tested 4 times. Frozen and stored samples were used, some of which were old and somewhat degraded. The titers of each sample were not determined. The FAM fluorescence was measured and the results in Table 5 show the area under the curve. Two samples (UL029 and FML16) were retested using different aliquots because of the initially low values seen with these two samples. The low values are believed due to poor quality samples which had degraded because of their age.

As a further check of sensitivity, known amounts of strain TW183 were assayed as for the results in Table 5. The results are shown in Table 6, the values representing the area under the curve of the fluorescence.

TABLE 6

| EBs | Fluorescence | Fluorescence | Fluorescence | Fluorescence |
|---|---|---|---|---|
| NC | 476.4 | 378.2 | 192.6 | 218.6 |
| 1 | 391.8 | 1019.2 | 773.8 | 461.4 |
| 5 | 458.8 | 1766.2 | 197.8 | 872 |
| 10 | 413 | 1282.2 | 1347.6 | 311.6 |
| 50 | 4620.6 | 6397.4 | 3813.8 | 3024.4 |
| 100 | 10722.2 | 12096.8 | 10069.8 | 7149.4 |
| 1000 | 23229.4 | 24503 | 20957.2 | 20400.6 |
| 10000 | 23005.8 | 27251.6 | 35300 | 28883.6 |

EXAMPLE 4

Cross-reactivity of GroES-EL Primer, Bumper and Detector System

The cross-reactivity of the GroES-EL primer, bumper and detector system was tested by performing reactions as described in Example 1 on a variety of species other than *Chlamydia pneumoniae*. These assays were performed using the GroES-EL 3' end positioned restriction site set of primers, bumpers and detector (GroES-EL-3). The results are shown in Table 7.

TABLE 5

Strain Sensitivity of GroES-EL Primers, Probes and Bumpers

| Strain | Fluorescence | Fluorescence | Fluorescence | Fluorescence |
|---|---|---|---|---|
| AO3 | 25894 | 29017 | 28329 | 29394 |
| AR39 | 20622 | 24892 | 22370 | 28071 |
| AR388 | 26739 | 24961 | 20585 | 16656 |
| BAL15 | 25414 | 20856 | 29869 | 29567 |
| BAL16 | 35607 | 28702 | 21265 | 25426 |
| BAL37 | 28330 | 22315 | 18258 | 24888 |
| CMI | 7249 | 12465 | 19228 | 15089 |
| CWL011 | 14759 | 22014 | 9297 | 17325 |
| FML16 - 1 | 6318 | 8648 | 3107 | 14744 |
| FML16 - 2 | 802 | 1125 | 1296 | |
| FML16 - 3 | 1334 | 3682 | 2456 | |
| FML16 - 4 | 12395 | 10199 | 17669 | |
| FML16 - 5 | 9053 | 18578 | 16529 | |
| UL029 - 1 | 369 | 243 | 51 | 283 |
| UL029 - 2 | 21417 | 26404 | 24821 | 22467 |
| UL029 - 3 | 21934 | 23030 | 18430 | 15239 |
| UL029 - 4 | 1967 | 2245 | 800 | 814 |
| UR1310 | 15261 | 22017 | 11480 | 27148 |
| 2023 | 29182 | 27442 | 13493 | 34176 |
| 2024 | 19954 | 19799 | 9964 | 24940 |
| 12368 | 21228 | 26265 | 9934 | 28133 |
| IOL1515 | 17196 | 29671 | 15419 | 28035 |
| U1271 | 25152 | 17333 | 25696 | 26652 |
| U1272 | 16148 | 15507 | 16160 | 19057 |
| AL1 | 14748 | 15954 | 15490 | 24502 |
| U172 | 14530 | 10878 | 10604 | 12824 |
| T45953 | 19660 | 18325 | 14573 | 14604 |
| U1273 | 20289 | 21016 | 15186 | 21426 |
| Negative control | 0 | 124 | 0 | 170 |
| Negative control | 313 | 386 | 31 | 144 |
| Negative control | 679 | 228 | 78 | 9 |

TABLE 7

Cross-reactivity of GroES-EL Primers, Bumpers and Detector

| | | | |
|---|---|---|---|
| Negative control | 65 | 33 | 43 |
| *E. aeruginosa* | 264 | 0 | 196 |
| *S. marcescens* | 197 | 70 | 170 |
| *St. agalactae* | 323 | 712 | 161 |
| *M. avium* | 0 | 0 | 100 |
| *M. intracellulare* | 217 | 115 | 10 |
| *M. tuberculosis* | 296 | 105 | 81 |
| *C. glabrate* | 523 | 268 | 340 |
| *Staph. epidermidis* | 82 | 322 | 238 |
| *St. faecalis* | 128 | 463 | 22 |
| *P. aeruginosa* | 241 | 137 | 244 |
| *Ent. cloacae* | 53 | 236 | 20 |
| *St. pneumoniae* | 0 | 266 | 32 |
| *C. albicans* | 102 | 237 | 428 |
| *K. pneumoniae* | 127 | 8 | 299 |
| *P. mirabilis* | 76 | 252 | 327 |
| *H. influenzae* | 376 | 410 | 438 |
| *Ac. lwoffi* | 268 | 517 | 486 |
| *E. coli* | 10 | 206 | 399 |
| *P. gingivalis* | 286 | 483 | 173 |
| *D. fragilis* | 28 | 245 | 137 |
| *E. histolytica* | 411 | 181 | 191 |
| *C. psittaci* - 1 | 192 | 3 | 261 |
| *C. psittaci* - 2 | 0 | 327 | 436 |
| *C. trachomatis* - 1 | 125 | 483 | 268 |
| *C. trachomatis* - 2 | 457 | 377 | 99 |
| *N. gonorrhoeae* | 689 | 385 | 61 |
| *T. vaginalis* | 506 | 30 | 723 |
| Positive control | 12395 | 10199 | 17669 |

While the invention has been described with some specificity, modifications apparent to those of ordinary skill in the art may be made without departing from the scope of the invention. Various features of the invention are set forth in the following claims.

What is claimed is:

1. An oligonucleotide consisting of a target binding sequence selected from the group consisting of the target binding sequences SEQ ID NO:1, SEQ ID NO:2, SEQ ID NO:6, SEQ ID NO:7, SEQ ID NO:11 and SEQ ID NO:12, and optionally, a sequence required for an amplification reaction.

2. The oligonucleotide of claim I wherein the sequence required for the amplification reaction is a restriction endonuclease recognition site which is nicked by a restriction endonuclease during Strand Displacement Amplification.

3. The oligonucleotide of claim 2 selected from the group consisting of SEQ ID NO:1, SEQ ID NO:2, SEQ ID NO:6, SEQ ID NO:7, SEQ ID NO:11 and SEQ ID NO:12.

4. An oligonucleotide consisting of SEQ ID NO:3.

5. An oligonucleotide consisting of a sequence selected from the group consisting of SEQ ID NO:5, a nucleic acid complementary to SEQ ID NO:5, SEQ ID NO:10, and a nucleic acid complementary to SEQ ID NO:10.

6. The nucleic acid of claim 5 wherein said nucleic acid comprises a detectable marker.

7. The nucleic acid of claim 6 wherein said detectable marker is selected from the group consisting of a radioactive marker and a fluorescence marker.

8. A pair of amplification primers comprising:

a) a first primer consisting of a target binding sequence selected from the group consisting of the target binding sequences of SEQ ID NO:1, SEQ ID NO:6 and SEQ ID NO:11, and, optionally, a sequence required for an amplification reaction, and;

b) a second primer consisting of a target binding sequence selected from the group consisting of the target binding sequences of SEQ ID NO:2, SEQ ID NO:7 and SEQ ID NO:12, and, optionally, a sequence required for an amplification reaction.

9. The pair of amplification primers of claim 8 wherein the sequence required for the amplification reaction is a restriction endonuclease recognition site which is nicked by a restriction endonuclease during Strand Displacement Amplification.

10. The pair of amplification primers of claim 9 wherein said first primer is selected from the group consisting of SEQ ID NO:1, SEQ ID NO:6 and SEQ ID NO:11 and said second primer is selected from the group consisting of SEQ ID NO:2, SEQ ID NO:7 and SEQ ID NO:12.

11. The pair of amplification primers of claim 9 wherein i) said first primer is SEQ ID NO:1 and said second primer is SEQ ID NO:2, ii) said first primer is SEQ ID NO:6 and said second primer is SEQ ID NO:7, or iii) said first primer is SEQ ID NO:11 and said second primer is SEQ ID NO:12.

12. A kit comprising:

a) one or more primers selected from the group consisting of SEQ ID NO:1, SEQ ID NO:6 and SEQ ID NO:11, b) one or more primers selected from the group consisting of SEQ ID NO:2, SEQ ID NO:7 and SEQ ID NO:12, c) bumpers i) SEQ ID NO:3, SEQ ID NO:8 or SEQ ID NO:13 and ii) SEQ ID NO:4, SEQ ID NO:9 or SEQ ID NO: 14, and d) one or more detectors selected from the group consisting of SEQ ID NO:5, a nucleic acid complementary to SEQ ID NO:5, SEQ ID NO:10, and a nucleic acid complementary to SEQ ID NO:10.

13. The kit of claim 12 wherein said one or more detectors comprises a detectable marker.

14. The kit of claim 13 wherein said detectable marker is selected from the group consisting of a radioactive marker and a fluorescence marker.

15. A method for detecting the presence or absence of *Chlamydia pneumoniae* in a sample, said method comprising the steps of:

a) treating said sample using a pair of nucleic acid primers in a nucleic acid amplification reaction wherein a first primer is selected from the group consisting of SEQ ID NO:1, SEQ ID NO:6 and SEQ ID NO:11 and a second primer is selected from the group consisting of SEQ ID NO:2, SEQ ID NO:7 and SEQ ID NO:12, and b) detecting any amplified nucleic acid product, wherein detection of amplified product indicates presence of *Chlamydia pneumoniae*.

16. The method of claim 15 wherein said nucleic acid amplification reaction is a Strand Displacement Amplification (SDA) reaction.

17. The method of claim 16 wherein said SDA reaction utilizes i) SEQ ID NO:3, SEQ ID NO:8 or SEQ ID NO:13 and ii) SEQ ID NO:4, SEQ ID NO:9 or SEQ ID NO:14 as bumpers.

18. The method of claim 15 wherein detecting said amplified nucleic acid product is conducted by hybridizing said amplified nucleic acid product with a detector selected from the group consisting of SEQ ID NO:5, a nucleic acid complementary to SEQ ID NO:, SEQ ID NO:10, and a nucleic acid complementary to SEQ ID NO:10.

19. The method of claim 16 wherein said SDA reaction is a thermophilic Strand Displacement Amplification (tSDA) reaction.

20. The method of claim 19 wherein said tSDA reaction is a homogeneous fluorescent real time tSDA reaction.

21. The method of claim 15 wherein the first primer is SEQ ID NO:1, SEQ ID NO:6 or SEQ ID NO:11 and the second primer is SEQ ID NO:2, SEQ ID NO:7 or SEQ ID NO:12.

22. A method for amplifying a target nucleic acid sequence of *Chlamydia pneumoniae* comprising:

a) hybridizing to the nucleic acid i) a first amplification primer consisting of a target binding sequence selected from the group consisting of the target binding sequences of SEQ ID NO:1, SEQ ID NO:6 and SEQ ID NO:11, and, optionally, a sequence required for an amplification reaction, and ii) a second amplification primer consisting of a target binding sequence selected from the group consisting of the target binding sequences of SEQ ID NO:2, SEQ ID NO:7 and SEQ ID NO:12, and, optionally, a sequence required for the amplification reaction, and;

b) extending the hybridized first and second amplification primers on the target nucleic acid sequence whereby the target nucleic acid sequence is amplified.

23. The method of claim 22 further comprising detecting the amplified target nucleic acid by hybridization to a detector probe.

24. The method of claim 23 wherein the detector probe consists of SEQ ID NO:5, a nucleic acid complementary to SEQ ID NO:5, SEQ ID NO:10, and a nucleic acid complementary to SEQ ID NO:10, tagged with a detectable label.

25. The method of claim 22 wherein the sequence required for the amplification reaction is a recognition site for a restriction endonuclease that is nicked by the restriction endonuclease during Strand Displacement Amplification.

26. The method of claim 25 wherein the first amplification primer is selected from the group consisting of SEQ ID NO:1, SEQ ID NO:6 and SEQ ID NO:11 and the second amplification primer is selected from the group consisting of SEQ ID NO:2, SEQ ID NO:7 and SEQ ID NO:12.

27. The method of claim 26 wherein the hybridized first and second amplification primers are displaced from the target nucleic acid by extension of a first bumper primer consisting of i) SEQ ID NO:3, SEQ ID NO:8 or SEQ ID NO:13 and ii) a second bumper consisting of SEQ ID NO:4, SEQ ID NO:9 or SEQ ID NO:14.

28. The method of claim 22 wherein the target nucleic acid is amplified by the Polymerase Chain Reaction.

29. The method of claim 25 wherein said SDA reaction is a thermophilic Strand Displacement Amplification (tSDA) reaction.

30. The method of claim 29 wherein said tSDA reaction is a homogeneous fluorescent real time tSDA reaction.

31. The method of claim 25 wherein the first amplification primer is SEQ ID NO:1, SEQ ID NO:6 or SEQ ID NO:11 and the second primer is SEQ ID NO:2, SEQ ID NO:7 or SEQ ID NO:12.

32. The method of claim 31 wherein the hybridized first and second amplification primers are displaced from the target nucleic acid by extension of a first bumper primer SEQ ID NO:3, SEQ ID NO:8 or SEQ ID NO:13 and a second bumper primer SEQ ID NO:4, SEQ ID NO:9 or SEQ ID NO:14.

* * * * *